US00PP32996P2

(12) United States Plant Patent
Heuger

(10) Patent No.: US PP32,996 P2
(45) Date of Patent: Apr. 20, 2021

(54) ***HELLEBORUS* PLANT NAMED 'COSEH 6300'**

(50) Latin Name: *Helleborus x ericsmithii X Helleborus x hybridus*
Varietal Denomination: COSEH 6300

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/873,646

(22) Filed: May 27, 2020

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 6300', characterized by its upright to somewhat outwardly spreading and mounded plant habit; moderately vigorous growth habit; dark green-colored leaves; freely flowering habit; yellow green and green white-colored flowers with red purple to greyed purple-colored margins; and good garden performance.

2 Drawing Sheets

Figure 1:
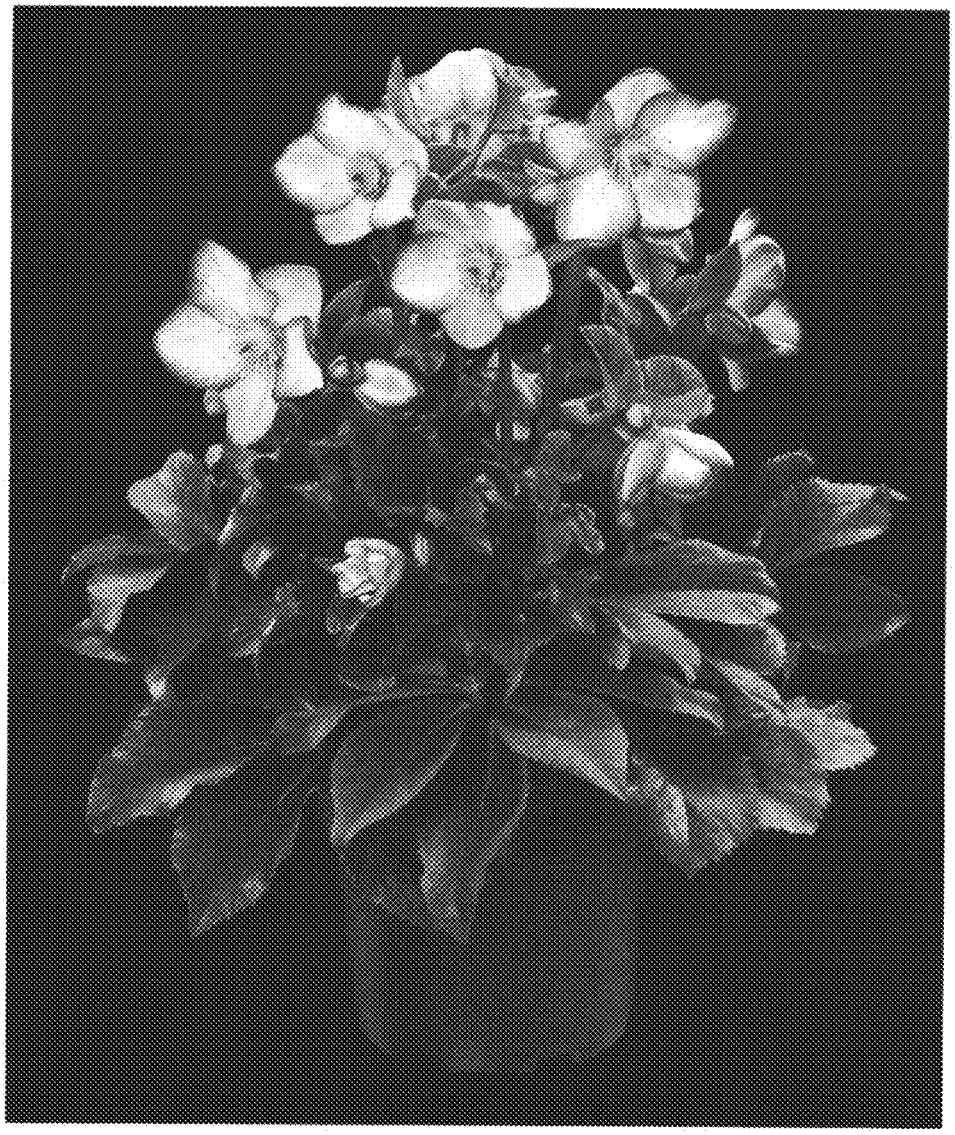

Botanical designation: *Helleborus* x *ericsmithii* X *Helleborus* x *hybridus*.
Cultivar denomination: 'COSEH 6300'

CROSS-REFERENCED TO CLOSELY-RELATED APPLICATIONS

Title: *Helleborus* Plant Named 'COSEH 6000'
Inventor/Applicant: Josef Heuger
Filed: Concurrently with the instant application Ser. No. 16/873,648
Title: *Helleborus* Plant Named 'COSEH 6100'
Inventor/Applicant: Josef Heuger
Filed: Concurrently with the instant application Ser. No. 16/873,647
Title: *Helleborus* Plant Named 'COSEH 7900'
Inventor/Applicant: Josef Heuger
Filed: Concurrently with the instant application Ser. No. 16/873,651
Title: *Helleborus* Plant Named 'COSEH 8000'
Inventor/Applicant: Josef Heuger
Filed: Concurrently with the instant application Ser. No. 16/873,650

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 6, 2019, application number 2019/1386. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 6300'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2012 of a proprietary selection of *Helleborus* x *ericsmithii* identified as code number P840, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in January, 2015.

Asexual reproduction of the new *Helleborus* plant by in vitro axillary meristem culture in a controlled environment in Glandorf, Germany since March, 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 6300'. These characteristics in combination distinguish 'COSEH 6300' as a new and distinct *Helleborus* plant:

1. Upright to somewhat outwardly spreading and mounded plant habit.
2. Moderately vigorous growth habit.
3. Dark green-colored leaves.
4. Freely flowering habit.
5. Yellow green and green white-colored flowers with red purple to greyed purple-colored margins.
6. Good garden performance.

Plants of the new *Helleborus* differ from plants of the female parent selection in the following characteristics:

1. Plants of the new *Helleborus* are more vigorous than plants of the female parent selection.
2. Flowers of plants of the new *Helleborus* are yellow green and green white in color with red purple to greyed purple-colored margins whereas flowers of plants of the female parent selection are greyed purple in color.

Plants of the new *Helleborus* differ from plants of the male parent selection in the following characteristics:

1. Plants of the new *Helleborus* are more vigorous than plants of the male parent selection.
2. Flowers of plants of the new *Helleborus* are yellow green and green white in color with red purple to greyed purple-colored margins whereas flowers of plants of the male parent selection are reddish in color.

Plants of the new *Helleborus* can be compared to plants of *Helleborus* x *ericsmithii* X *Helleborus* x *hybridus* 'COSEH 6000', disclosed in a U.S. Plant Patent application filed concurrently. Plants of the new *Helleborus* differ primarily from plants of 'COSEH 6000' in flower color as plants of the new *Helleborus* have yellow green and green white-colored flowers with red purple to greyed purple-colored margins whereas plants of 'COSEH 6000' have dark greyed purple-colored flowers.

Plants of the new *Helleborus* can be compared to plants of *Helleborus* x *ericsmithii* X *Helleborus* x *hybridus* 'COSEH 6100', disclosed in a U.S. Plant Patent application filed concurrently. Plants of the new *Helleborus* differ primarily from plants of 'COSEH 6100' in flower color as plants of the new *Helleborus* have yellow green and green white-colored flowers with red purple to greyed purple-colored margins whereas plants of 'COSEH 6100' have greyed purple to greyed red purple-colored flowers.

Plants of the new *Helleborus* can be compared to plants of *Helleborus* x *ericsmithii* X *Helleborus* x *hybridus* 'COSEH 7900', disclosed in a U.S. Plant Patent application filed concurrently. Plants of the new *Helleborus* differ primarily from plants of 'COSEH 7900' in flower color as plants of the new *Helleborus* have yellow green and green white-colored flowers with red purple to greyed purple-colored margins whereas plants of 'COSEH 7900' have greyed purple-colored flowers.

Plants of the new *Helleborus* can be compared to plants of *Helleborus* x *ericsmithii* X *Helleborus* x *hybridus* 'COSEH 8000', disclosed in a U.S. Plant Patent application filed concurrently. Plants of the new *Helleborus* differ primarily from plants of 'COSEH 8000' in flower color as plants of the new *Helleborus* have yellow green and green white-colored flowers with red purple to greyed purple-colored margins whereas plants of 'COSEH 8000' have greyed purple to dark purple-colored flowers.

Plants of the new *Helleborus* can also be compared to plants of *Helleborus* x *ericsmithii* X *Helleborus* x *hybridus* 'COSEH 4600', disclosed in U.S. Plant Pat. No. 30,488. In side-by-side comparisons, plants of the new *Helleborus* differ primarily from plants of 'COSEH 4600' in the following characteristics:

1. Plants of the new *Helleborus* are taller than plants of 'COSEH 4600'.
2. Plants of the new *Helleborus* differ from plants of 'COSEH 4600' in flower color as plants of the new *Helleborus* have yellow green and green white-colored flowers with red purple to greyed purple-colored margins whereas plants of 'COSEH 4600' have dark greyed purple-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 6300' grown in a container.

Figure 2:
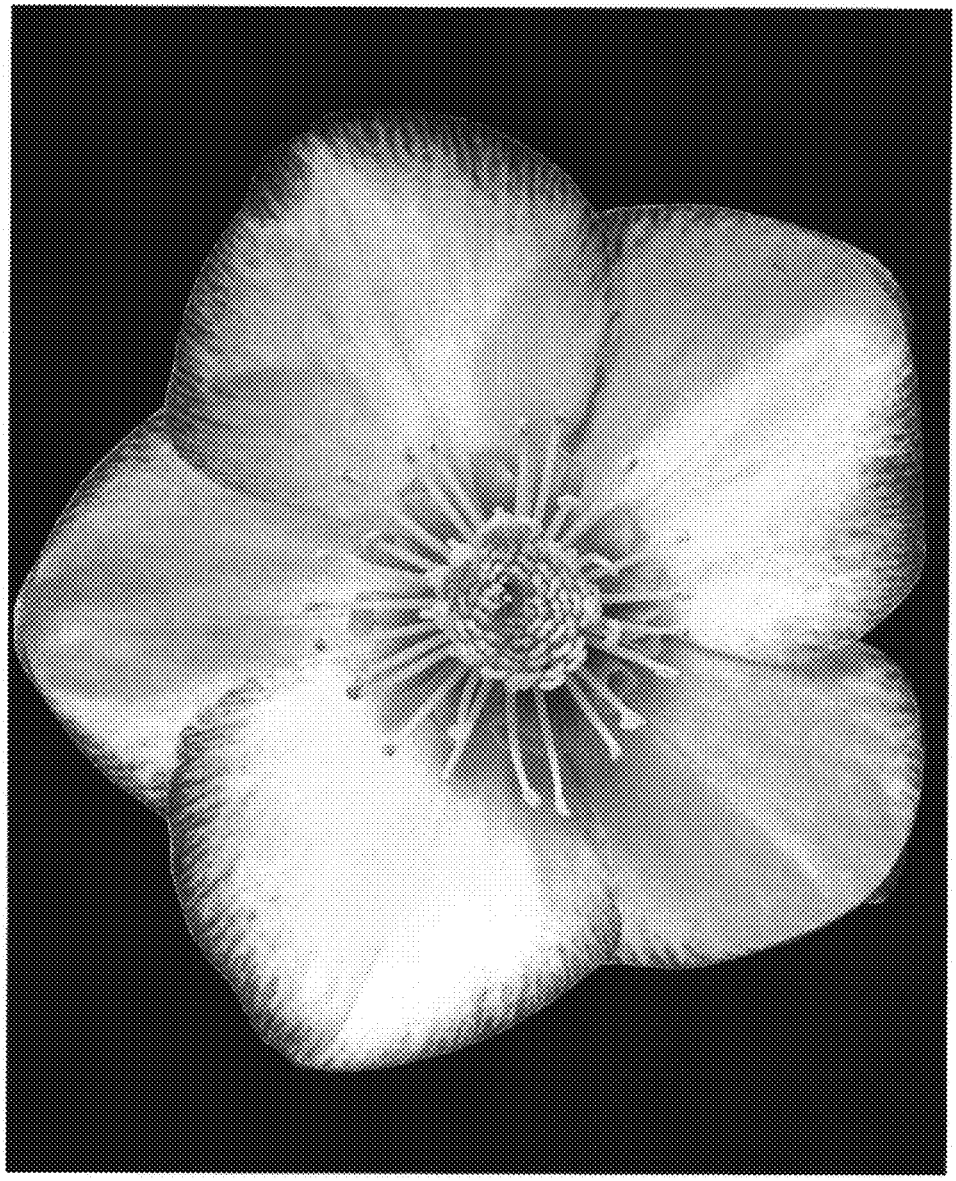

The photograph on the second sheet (FIG. 2 of 2) is a close-up view of a typical flower of 'COSEH 6300'.

DETAILED BOTANICAL DESCRIPTION

The aforementioned photographs and following observations, measurements and values describe plants grown during March in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 6300'.

Parentage:

*Female, or seed, parent.*—Proprietary selection of *Helleborus* x *ericsmithii* disclosed as code number P840, not patented.

*Male, or pollen, parent.*—Unnamed selection of *Helleborus* x *hybridus*, not patented.

Propagation:

*Type.*—In vitro axillary meristem culture.

*Time to initiate roots, winter.*—About 55 days at temperatures about 12° C.

*Time to produce a rooted young plant, winter.*—About 170 days at temperatures ranging from 4° C. to 15° C.

*Root description.*—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright and mounding plant habit with flowers held within and above the foliar plane; plant shape, broadly ovate; moderately vigorous growth habit and moderate growth rate.

*Plant height, soil level to top of foliar plane*.—About 32.2 cm.

*Plant height, soil level to top of flowers*.—About 39.4 cm.

*Plant diameter* (*area of spread*).—About 51.1 cm.

Leaf description:

*Arrangement*.—Leaves arranged in a basal rosette; leaves palmately compound with typically five leaflets per leaf.

*Leaf length*.—About 20.4 cm.

*Leaf width*.—About 22.4 cm.

*Leaflet length*.—About 13.8 cm.

*Leaflet width*.—About 6.4 cm.

*Leaf shape*.—Palmate; reniform in outline.

*Leaflet shape*.—Obovate to elliptic.

*Leaflet apex*.—Acute.

*Leaflet base*.—Attenuate.

*Leaflet margin*.—Serrate; when developing without undulation and developed leaves are coarsely undulate.

*Leaflet texture and luster, upper surface*.—Smooth, glabrous; leathery; moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to NN137B. Developing leaflets, lower surface: Close to between 146A and 147B; midvein, close to between 177A and 200C. Fully developed leaflets, upper surface: Darker than between 139A and 147A; venation, close to 144B to 144C, towards the base, close to N186C. Fully developed leaflets, lower surface: Slightly darker than 148A; venation, close to 187A.

*Petioles*.—Length: About 15.1 cm. Diameter: About 7 mm to 9 mm. Strength: Strong. Texture and luster, upper and lower surfaces: Smooth, glabrous; slightly glossy. Color, upper surface: Close to 144A to 144B moderately covered with fine dots, close to 183A. Color, lower surface: Close to 144A to 144B moderately to heavily covered with fine dots, close to 183A and proximally, closer to 184A.

Flower description:

*Flower shape and habit*.—Rotate flowers; flowers slightly cupped; arranged in panicles; freely flowering habit with about seven flowers per inflorescence and about 60 flowers developing per plant; flowers face mostly outwardly to slightly nodding.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 2 cm. Diameter: About 1.1 cm. Shape: Narrowly ovate to narrowly oblong. Texture and luster: Smooth, glabrous; matte. Color: Close to 145C distally tinged with close to 60D.

*Inflorescence height* (*including peduncle*).—About 36.6 cm.

*Inflorescence diameter*.—About 17.3 cm.

*Flower diameter*.—About 6.8 cm by 6.8 cm.

*Flower depth* (*height*).—About 2.4 cm.

*Petals*.—All petals are transformed into nectaries.

*Sepals*.—Quantity and arrangement: About five, arranged in a single whorl. Length: About 3.6 cm. Width: About 2.9 cm. Shape: Broadly elliptic to broadly obovate, slightly concave. Apex: Obtuse. Base: Truncate to broadly cuneate. Margin: Entire; slightly undulate. Texture and luster, upper surface: Smooth, glabrous; matte. Texture and luster, lower surface: Smooth, glabrous; slightly glossy. Color: When opening, upper surface: Close to 150D; towards the base, close to 145C; towards the apex, close to 60C to 60D. When opening, lower surface: Close to 150D; towards the base, close to 145B to 145C; towards the apex, close to 60C to 60D. Fully opened, upper surface: Close to 145D and 157A; towards the margins and apex, close to 60C; with development, color becoming closer to between 144B and 146D and towards the margins and apex, close to between N187A and N187B; venation, similar to lamina. Fully opened, lower surface: Close to 145D; towards the margins and apex, close to 60C; with development, color becoming closer to between 144C and 146D and towards the margins and apex, close to between N187A; venation, close to 187A.

*Flower bracts*.—Quantity per flower: Typically one or two. Length: About 3.8 cm. Width: About 2.9 cm. Shape: Ovate. Apex: Acute to tri-lobed or emarginate. Base: Truncate. Margin: Mostly entire; distally, finely serrate; slightly undulate. Color, upper surface: Close to 137A. Color, lower surface: Close to 147B; midvein tinged with close to 177A.

*Peduncles*.—Length: About 30.1 cm. Diameter: About 7 mm. Aspect: About 10° from vertical. Strength: Strong. Texture and luster: Smooth, glabrous; glossy. Color: Close to 144B, heavily covered with fine dots, close to 184B.

*Pedicels*.—Length: About 2.5 cm. Diameter: About 2 mm. Aspect: About 10° to 25° from peduncle axis. Strength: Moderately strong. Texture and luster: Smooth, glabrous; glossy. Color: Close to 145A.

*Reproductive organs*.—Stamens: Quantity per flower: About 60. Filament length: About 1.6 cm. Filament color: Close to NN155A. Anther shape: Double and broadly reniform; basifixed. Anther size: About 2 mm by 3 mm. Anther color: Close to 150C. Pollen amount: Moderate. Pollen color: Close to 4D to lighter than 4D. Pistils: Quantity per flower: About five or occasionally six or seven. Pistil length: About 1 cm. Stigma diameter: About 0.3 mm. Stigma shape: Club-shaped. Stigma color: Close to 155C. Style length: About 9 mm. Style color: Close to 60D. Ovary color: Close to between 145C and 150D. Nectaries (transformed petals): Quantity per flower: About 13. Length: About 1.1 cm. Diameter: About 3.5 mm. Shape: Tubular, flattened. Texture and luster, inner and outer surfaces: Smooth, glabrous; slightly glossy. Color, immature, inner surface: Close to N144D. Color, immature, outer surface:

Close to N144D; spot at base, close to N144A. Color, mature, inner surface: Close to 154B; with development, becoming closer to 154A and towards the base, close to N144C; venation, similar to lamina. Color, mature, outer surface: Close to 154B; spot at base, close to 152D; with development, becoming closer to 154A, towards the base, close to N144C and spot, closer to 152C; venation, similar to lamina.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 6300' as illustrated and described.

* * * * *